United States Patent
Xu

(10) Patent No.: US 11,559,265 B2
(45) Date of Patent: Jan. 24, 2023

(54) SYSTEMS AND METHODS FOR ADJUSTING MEDICAL DEVICE

(71) Applicant: SHANGHAI UNITED IMAGING HEALTHCARE CO., LTD., Shanghai (CN)

(72) Inventor: Lu Xu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 16/988,780

(22) Filed: Aug. 10, 2020

(65) Prior Publication Data
US 2020/0367840 A1 Nov. 26, 2020

Related U.S. Application Data

(63) Continuation of application No. 15/681,327, filed on Aug. 18, 2017, now Pat. No. 10,736,586.

(30) Foreign Application Priority Data

Aug. 14, 2017 (CN) .......................... 201710693821.1

(51) Int. Cl.
| | | |
|---|---|---|
| A61B 6/00 | (2006.01) | |
| A61N 5/10 | (2006.01) | |
| G16H 40/63 | (2018.01) | |
| G06T 7/70 | (2017.01) | |
| G16H 30/20 | (2018.01) | |

(Continued)

(52) U.S. Cl.
CPC .............. *A61B 6/102* (2013.01); *A61B 6/027* (2013.01); *A61B 6/032* (2013.01); *A61B 6/5205* (2013.01);
(Continued)

(58) Field of Classification Search
CPC ......... A61B 6/102; A61B 6/027; A61B 6/032; A61B 6/5205; A61B 6/547; A61B 6/4085;
(Continued)

(56) References Cited

U.S. PATENT DOCUMENTS

| | | | |
|---|---|---|---|
| 4,578,757 A | 3/1986 | Stark | |
| 10,549,116 B2 * | 2/2020 | Sheng | .................. A61N 5/1082 |

(Continued)

FOREIGN PATENT DOCUMENTS

| | | |
|---|---|---|
| CN | 105983183 A | 10/2016 |
| CN | 106621075 A | 5/2017 |
| EP | 2944261 A1 | 11/2015 |

OTHER PUBLICATIONS

James T. Klosowski et al., Efficient Collision Detection Using Bounding vol. Hierarchies of k-DOPs, IEEE Transactions on Visualization and Computer Graphics, 4 (1): 21-36, 1998.

(Continued)

*Primary Examiner* — David P Porta
*Assistant Examiner* — Jeremy S Valentiner
(74) *Attorney, Agent, or Firm* — Metis IP LLC

(57) ABSTRACT

A method for adjusting a medical device is provided. The method includes obtaining an initial trajectory of a component of the medical device. The initial trajectory of the component includes a plurality of initial positions. For each of the plurality of initial positions, the method further includes determining whether a collision is likely to occur between a subject and the component according to the initial trajectory of the component. In response to the determination that the collision is likely to occur, the method further includes updating the initial trajectory of the component to determine an updated trajectory of the component.

18 Claims, 11 Drawing Sheets

(51) Int. Cl.
   *A61B 6/10* (2006.01)
   *A61B 6/03* (2006.01)
   *A61B 6/02* (2006.01)
(52) U.S. Cl.
   CPC .............. *A61B 6/547* (2013.01); *A61N 5/103* (2013.01); *G06T 7/70* (2017.01); *G16H 40/63* (2018.01); *A61B 6/4085* (2013.01); *A61N 5/1045* (2013.01); *A61N 5/1049* (2013.01); *G06T 2207/30241* (2013.01); *G16H 30/20* (2018.01)
(58) Field of Classification Search
   CPC . G06T 7/70; G06T 2207/30241; G16H 40/63; G16H 30/20; A61N 5/103; A61N 5/1045; A61N 5/1049
   See application file for complete search history.

(56) References Cited

U.S. PATENT DOCUMENTS

| | | |
|---|---|---|
| 2004/0044265 A1 | 3/2004 | Muller et al. |
| 2006/0173273 A1* | 8/2006 | Boese ..................... A61B 5/103 600/407 |
| 2008/0187097 A1* | 8/2008 | Cheng ..................... B25J 9/1666 378/65 |
| 2009/0067577 A1 | 3/2009 | Rigney et al. |
| 2009/0080619 A1 | 3/2009 | Hasegawa et al. |
| 2010/0027742 A1* | 2/2010 | Movassaghi ......... A61B 6/4441 378/197 |
| 2012/0296148 A1 | 11/2012 | Nord et al. |
| 2015/0035942 A1* | 2/2015 | Hampton ............. A61N 5/1049 348/42 |
| 2016/0161938 A1 | 6/2016 | Popple et al. |
| 2016/0302871 A1* | 10/2016 | Gregerson ............. A61B 34/20 |
| 2016/0325117 A1 | 11/2016 | Arai |
| 2017/0086758 A1 | 3/2017 | McCarthy et al. |
| 2018/0318420 A1* | 11/2018 | Takeyoshi ............ A61N 5/1077 |

OTHER PUBLICATIONS

Arthur Boyer et al., Basic Applications of Multileaf Collimators, American Association of Physicists in Medicine Report No. 72, Medicai Physics Publishing, 2001, 62 pages.
First Office Action in Chinese Application No. 201710693821.1 dated Jan. 20, 2020, 39 pages.

* cited by examiner

SYSTEMS AND METHODS FOR ADJUSTING MEDICAL DEVICE

CROSS-REFERENCE TO RELATED APPLICATIONS

This application is a continuation of U.S. application Ser. No. 15/681,327, filed on Aug. 18, 2017, which claims priority of Chinese Application No. 201710693821.1 filed on Aug. 14, 2017, and the entire contents of these two prior applications are hereby incorporated by reference.

TECHNICAL FIELD

This disclosure generally relates to optical devices, and more particularly, to a lens system and an imaging device with the lens system.

BACKGROUND

Lenses play an important role in the field of security monitoring. The lenses in a camera receive rays that are reflected by an object and project the rays to an imaging sensor in the camera to generate an image of the object. The performance of the lenses may affect the image quality, which may affect the accuracy of the result in the security monitoring. The apertures and image planes of some existing lenses used in the security monitoring are relatively small, and the existing lenses cannot achieve a constant aperture, which decreases the image quality. Therefore, it is desirable to provide a lens system that can achieve a relatively large constant aperture and a relatively large image plane.

SUMMARY

According to an aspect of the present disclosure, a system is provided. The system may include a storage device storing a set of instructions and at least one processor in communication with the storage device. When executing the set of instructions, the at least one processor may be configured to cause the system to: obtain an initial trajectory of a component of a medical device, wherein the initial trajectory of the component includes a plurality of initial positions; and for each of the plurality of initial positions, determine whether a collision is likely to occur between a subject and the component according to the initial trajectory of the component, and in response to determining that the collision is likely to occur between the subject and the component, update the initial trajectory of the component to determine an updated trajectory of the component.

In some embodiments, to determine whether the collision is likely to occur between a subject and the component of the medical device, the at least one processor may be further configured to cause the system to determine, during a movement of the component, whether the collision is likely to occur between a subject and the component.

In some embodiments, to determine whether the collision is likely to occur between a subject and the component of the medical device, the at least one processor may be further configured to cause the system to determine, before or after a movement of the component, whether the collision is likely to occur between a subject and the component.

In some embodiments, the at least one processor may be further configured to cause the system to determine one or more parameters associated with the updated trajectory of the component, the one or more parameters including at least one of a velocity, a moving direction, a position, or an accelerated velocity.

In some embodiments, to update the initial trajectory of the component to determine the updated trajectory of the component, the at least one processor may be further configured to cause the system to update at least one of an initial position of the component in the initial trajectory of the component, or an initial orientation of the component in the initial trajectory of the component.

According to another aspect of the present disclosure, a system is provided. The system may include a storage device storing a set of instructions and at least one processor in communication with the storage device. When executing the set of instructions, the at least one processor may be configured to cause the system to: obtain an initial trajectory of a component of a CBCT device, the component including a detector or a scanning source, wherein the initial trajectory of the component includes a plurality of initial positions; and for each of the plurality of initial positions, determine whether a collision is likely to occur between a subject and the component according to the initial trajectory of the component, and in response to the determination that the collision is likely to occur between the subject and the component, update the initial trajectory of the component to determine an updated trajectory of the component.

In some embodiments, to determine whether the collision is likely to occur between a subject and the component of the CBCT device, the at least one processor may be further configured to cause the system to determine, during a movement of the component, whether the collision is likely to occur between a subject and the component.

In some embodiments, to determine whether the collision is likely to occur between a subject and the component of the CBCT device, the at least one processor may be further configured to cause the system to determine, before or after a movement of the component, whether the collision is likely to occur between a subject and the component.

According to another aspect of the present disclosure, a system is provided. The system may include a storage device storing a set of instructions and at least one processor in communication with the storage device. When executing the set of instructions, the at least one processor may be configured to cause the system to: obtain an initial trajectory of a component of a radiotherapy (RT) device, the component including an irradiation head or an electronic portal imaging device (EPID), wherein the initial trajectory of the component includes a plurality of initial positions; and for each of the plurality of initial positions, determine whether a collision is likely to occur between a subject and the component according to the initial trajectory of the component, and in response to the determination that the collision is likely to occur between the subject and the component, update the initial trajectory of the component to determine an updated trajectory of the component.

In some embodiments, to determine whether the collision is likely to occur between a subject and the component of the RT device, the at least one processor may be further configured to cause the system to determine, during a movement of the irradiation head, whether the collision is likely to occur between a subject and the component.

In some embodiments, to determine whether the collision is likely to occur between a subject and the component of the RT device, the at least one processor may be further configured to cause the system to determine, before or after a movement of the irradiation head, whether the collision is likely to occur between a subject and the component.

In some embodiments, the irradiation head may include a shell, a target, a primary collimator, jaws, or a multi-leaf collimator. The multi-leaf collimator may be configured inside the shell of the irradiation head. To update the initial trajectory of the irradiation head, the at least one processor may be further configured to cause the system to update an initial trajectory of at least the shell.

In some embodiments, the multi-leaf collimator may be configure outside the shell of the irradiation head. To update the initial trajectory of the irradiation head, the at least one processor may be further configured to cause the system to determine whether the collision is likely to occur between the subject and the multi-leaf collimator.

In some embodiments, to update the initial trajectory of the irradiation head, the at least one processor may be further configured to cause the system to update an initial trajectory of at least the multi-leaf collimator and adjust a beam field defined by the multi-leaf collimator.

According to another aspect of the present disclosure, a method is provided. The method may be implemented on a system. The system may include at least one processor and a storage device. The method may include: obtaining an initial trajectory of a component of a medical device, wherein the initial trajectory of the component includes a plurality of initial positions; and for each of the plurality of initial positions, determining whether a collision is likely to occur between a subject and the component according to the initial trajectory of the component, and in response to the determination that the collision is likely to occur between the subject and the component, updating the initial trajectory of the component to determine an updated trajectory of the component.

According to another aspect of the present disclosure, a non-transitory computer readable medium is provided. The non-transitory computer readable medium may embody a computer program product that includes instructions configured to cause a computing system to: obtain an initial trajectory of a component of a medical device, wherein the initial trajectory of the component includes a plurality of initial positions; and for each of the plurality of initial positions, determine whether a collision is likely to occur between a subject and the component according to the initial trajectory of the component, and in response to the determination that the collision is likely to occur between the subject and the component, update the initial trajectory of the component to determine an updated trajectory of the component.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1A:
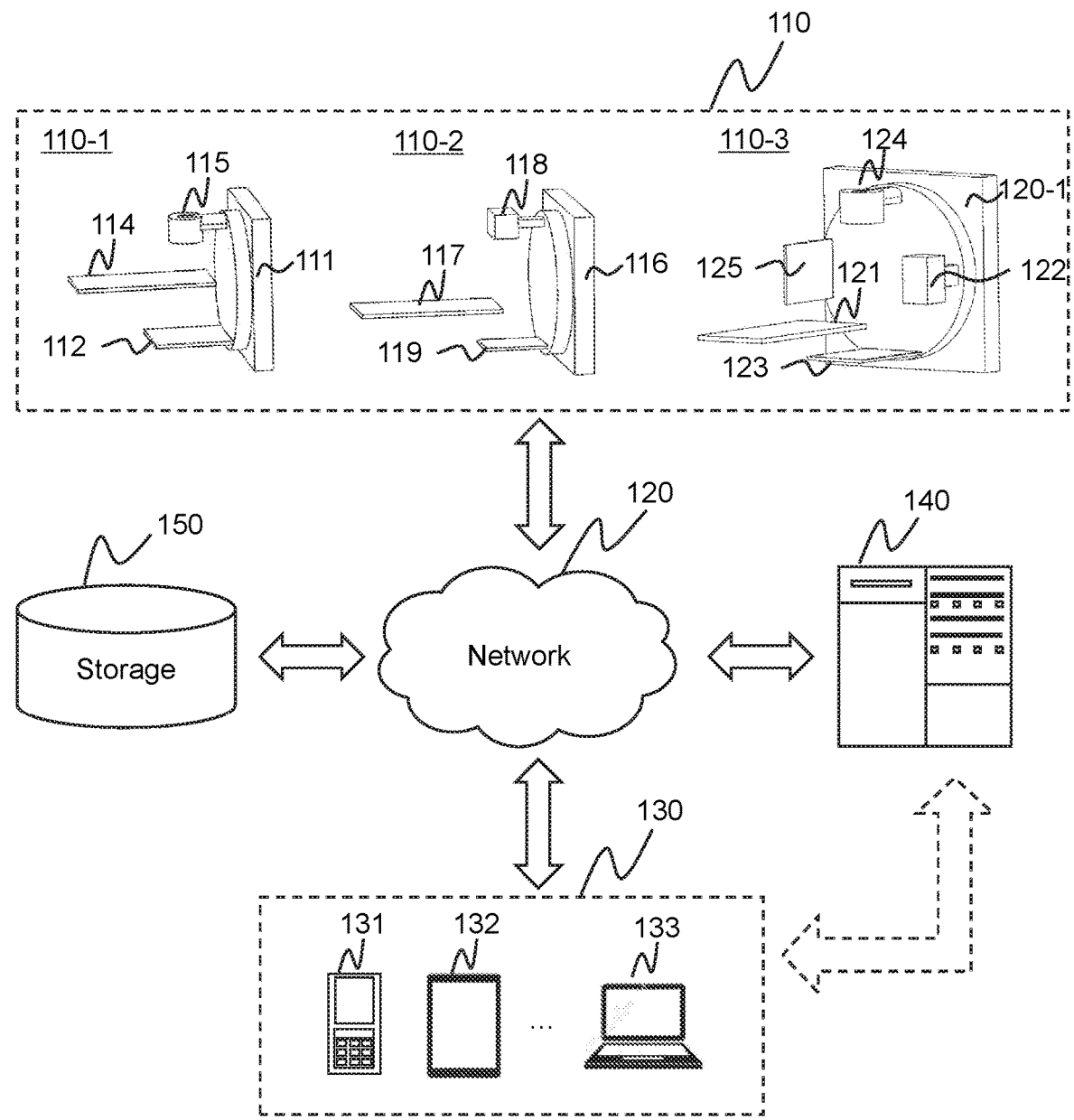
FIGS. 1A and 1B are schematic diagrams illustrating an exemplary system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order.

However, the terms may be displaced by other expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., CPU 220 illustrated in FIG. 2) may be provided on a computer-readable medium, such as a compact disc, a digital video disc, a flash drive, a magnetic disc, or any other tangible medium, or as a digital download (and can be initially stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for adjusting a geometry of a medical device and/or obtaining image data according to the adjusted geometry. In some embodiments, the medical device may include a computed tomography (CT), a Cone Beam Computed Tomography (CBCT), an emission computed tomography (ECT), a magnetic resonance imaging (MRI), a radiotherapy (RT) device, or the like, or any combination thereof.

The following description is provided to help better understanding CT image reconstruction methods and/or systems. The term "image" used in this disclosure may refer to a 2D image, a 3D image, a 4D image, and/or any related image data (e.g., CT data, projection data corresponding to the CT data). This is not intended to limit the scope the present disclosure. For persons having ordinary skills in the art, processes and/or applications in the CT image reconstruction may also be applicable in other modal imaging systems described above.

Moreover, the system and method in the present disclosure is described primarily in regard to avoiding a collision between a component of a medical device and a patient. In some embodiments, the system and the method may determine whether a collision between the component of the medical device and the patient is likely to occur. In some embodiments, the system and the method may further adjust the geometry of the medical device in responding to the determination that a collision is likely to occur. Adjusting the geometry of the medical device may include update a trajectory of the component of the medical device.

Figure 1B:
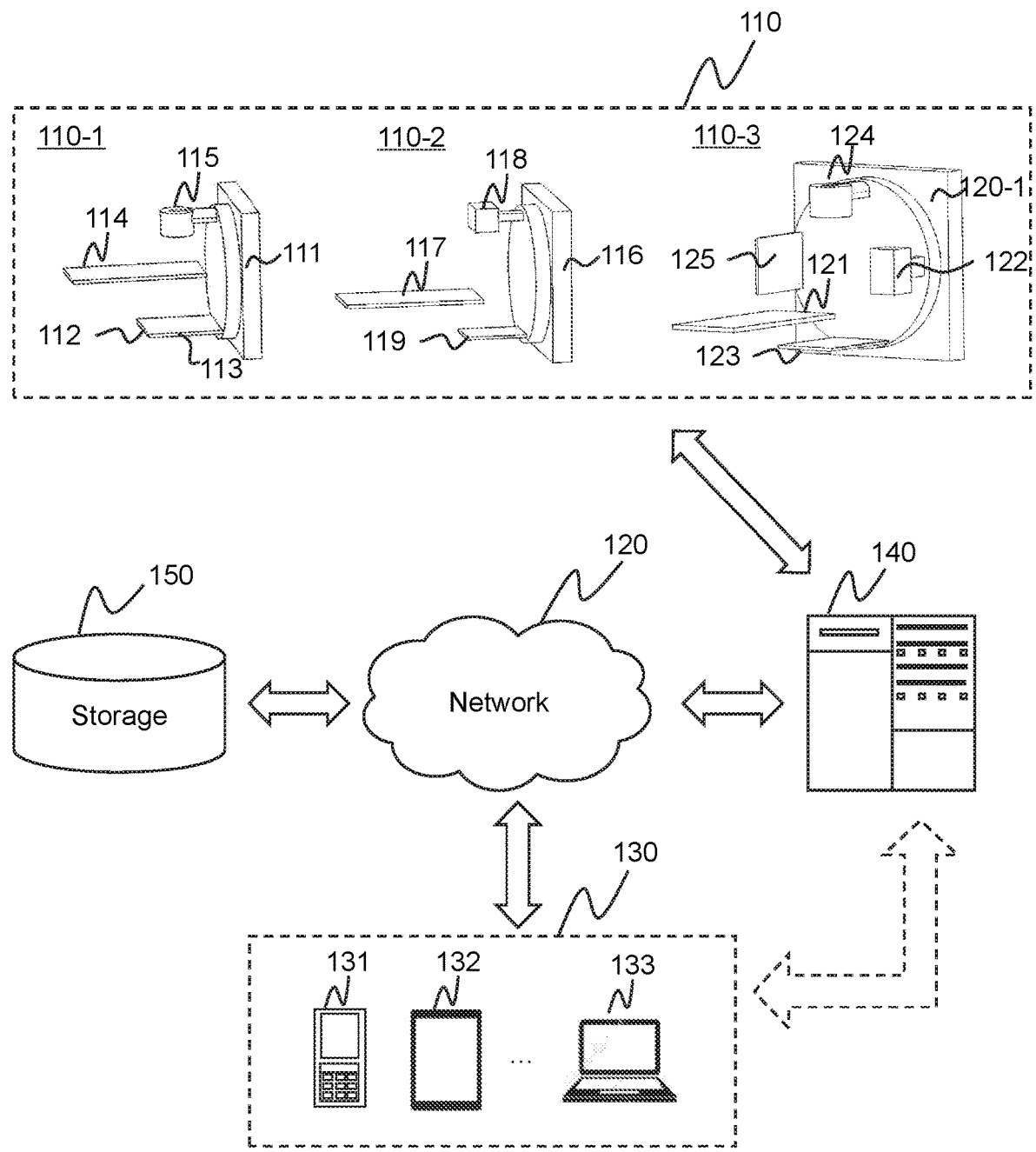

FIGS. 1A and 1B are schematic diagrams illustrating an exemplary medical system 100 according to some embodiments of the present disclosure. In some embodiments, the medical system 100 may include a medical device 110, a network 120, one or more terminals 130, a processing device 140, and a storage 150.

In some embodiments, the medical device 110 may include a CBCT device 110-1. The CBCT device 110-1 may include a gantry 111, a detector 112, a table 114, and a scanning source 115. The gantry 111 may support the detector 112 and the scanning source 115. A subject may be placed on the table 114 for scanning. The scanning source 115 may emit a cone beam of X-rays to a subject. The detector 112 may detect attenuated X-rays. The attenuated X-rays may be processed and converted to image data.

Figure 9A:
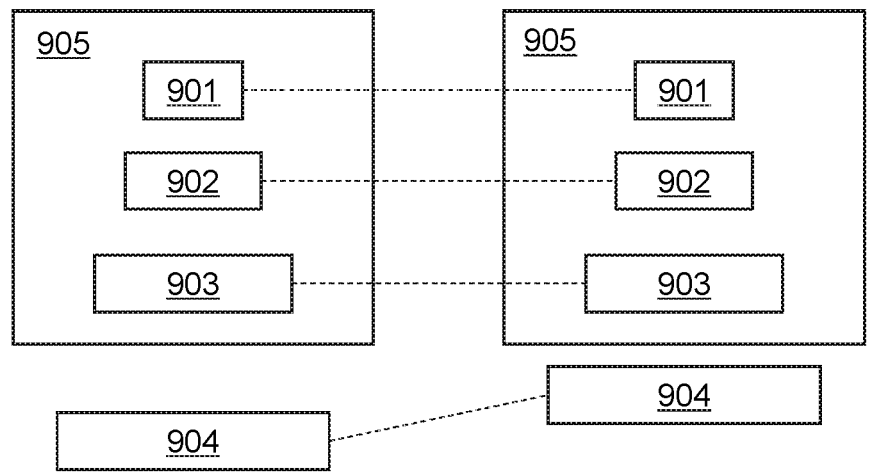
FIGS. 9A through 9D illustrate exemplary position updating of one or more components of a radiotherapy device according to some embodiments of the present disclosure.
Figure 9B:
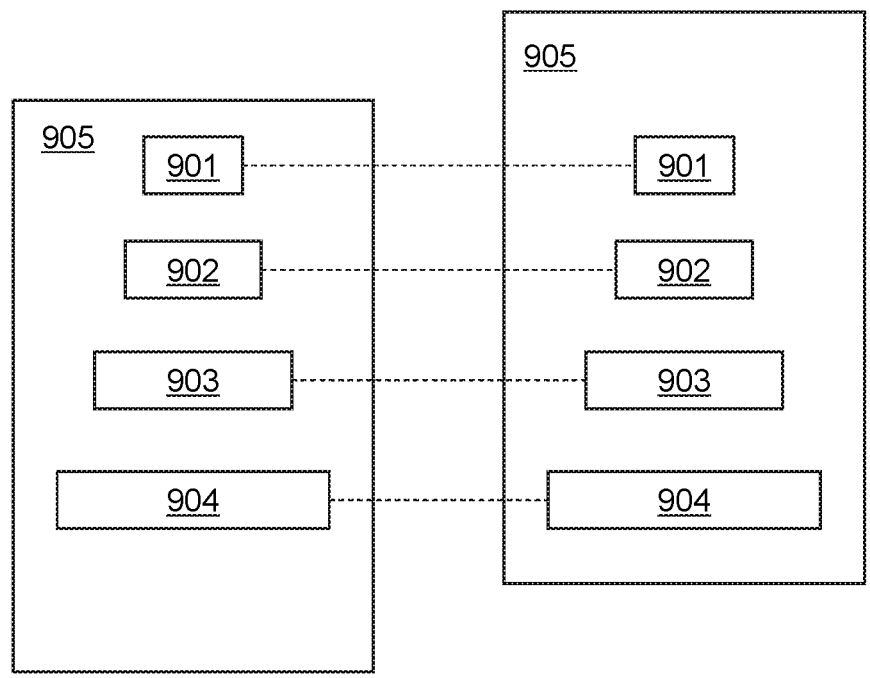
Figure 9C:
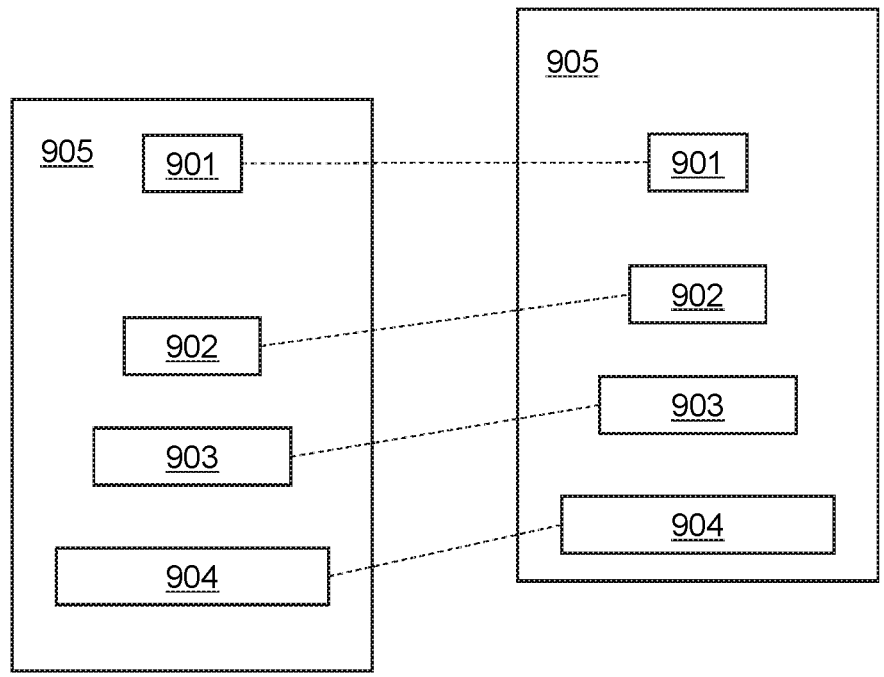
Figure 9D:
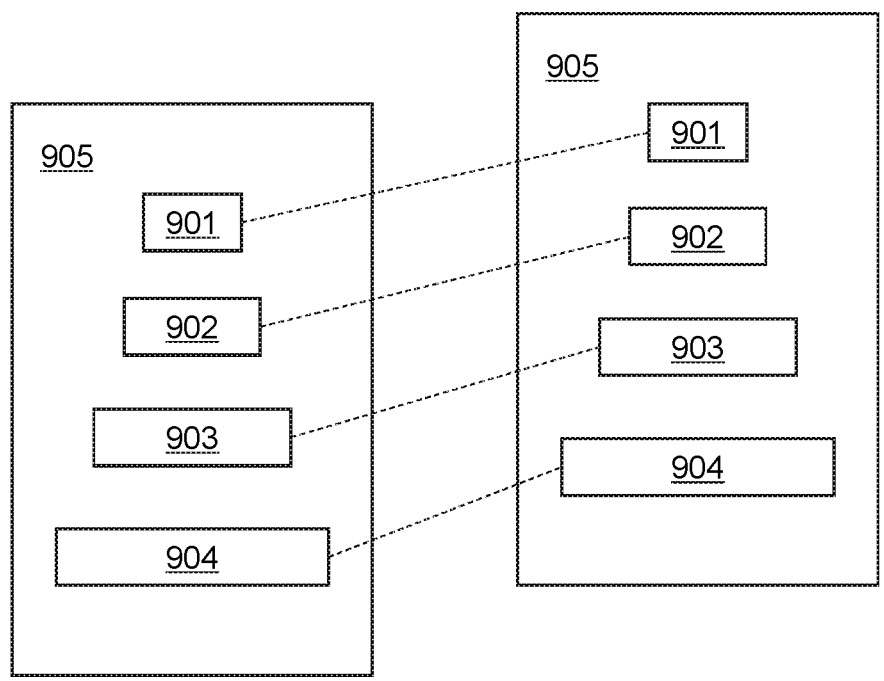

In some embodiments, the medical device 110 may include a radiotherapy (RT) device 110-2. The RT device 110-2 may include a gantry 116, a table 117, and an irradiation head 118, an electronic portal imaging device (EPID) 119. The irradiation head 118 may include a target (e.g., target 901 shown in FIG. 9A), a primary collimator (e.g., primary collimator 902 shown in FIG. 9A), jaws (e.g., jaws 903 shown in FIG. 9A), a multi-leaf collimator (MLC) (e.g., MLC 904 shown in FIG. 9A), and a shell (e.g., shell 905 shown in FIG. 9A) configured to cover one or more components of the irradiation head. Specifically, the MLC may be inside or outside the shell. For example, the MLC 904 is inside the shell 905 as illustrated in FIGS. 9B through 9D. As another example, the MLC 904 is outside the shell 905 as illustrated in FIG. 9A. Accelerated particles may impinge the target 901 to generate radiation. The radiation may include photon beam, electron beam, proton beam, etc. The radiation may be shaped into a desirable beam through the primary collimator 902, the jaws 903, and the multi-leaf collimator 904. The desirable beam may be directed to a subject to carry out a treatment plan.

In some embodiments, the medical device 110 may include a combination of a CBCT device and an RT device (also referred to herein as CBCT-RT device 110-3). The CBCT-RT device 110-3 may include a gantry 120-1, a table 121, an irradiation head 122, a detector 123, a scanning source 124, an EPID 125, etc. In some embodiments, the CBCT-RT device 110-3 may not include an EPID. The CBCT-RT device 110-3 may perform scanning and treatment successively or simultaneously.

The network 120 may include any suitable network that can facilitate exchange of information and/or data for the medical system 100. In some embodiments, one or more components of the medical system 100 (e.g., the medical device 110, the terminal 130, the processing device 140, the storage 150) may communicate with one or more other components of the medical system 100 via the network 120. For example, the processing device 140 may obtain image data from the medical device 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a Zig-Bee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the medical system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™. In some embodiments, the terminal(s) 130 may be part of the processing device 140.

The processing device 140 may detect whether a collision between a component of the medical device 110 and a subject is likely to occur. In responding to the determination that the collision between the component and the subject is likely to occur, the processing device 140 may adjust the geometry of the medical device 110. For example, the processing device 140 may update a trajectory of the component. More particularly, the processing device 140 may update the position of the component, update the orientation of the component, or the like, or a combination thereof. In some embodiments, the processing device 140 may determine an updated trajectory of the component. For example, the processing device 140 may determine the updated trajectory based on a machine-learning technique. More particularly, the processing device 140 may select one of a plurality of existing trajectories of the component as the updated trajectory based on one or more features of the subject.

In some embodiments, the processing device 140 may be a single server or a server group. The server group may be centralized or distributed. In some embodiments, the processing device 140 may be local or remote from other components in the medical system 100. The processing device 140 may access trajectories of components of the medical device 110 stored in the medical device 110, the terminal 130, and/or the storage 150 via the network 120. Alternatively, the processing device 140 may be directly connected to the medical device 110, the terminal 130 and/or the storage 150 to access stored trajectories. In some embodiments, the processing device 140 may be implemented on a cloud platform to perform processing. For example, the processing device 140 may be implemented on the cloud platform to detect whether a collision between a component of the medical device 110 and a subject, adjust the geometry of the medical device 110, perform trajectory planning, or the like, or a combination thereof. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage 150 may store data, instructions, and/or any other information. In some embodiments, the storage 150 may store data obtained from the terminal 130 and/or the processing device 140. In some embodiments, the storage 150 may store data and/or instructions that the processing device 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the medical system 100 (e.g., the processing device 140, the terminal 130). One or more components of the medical system 100 may access the data or instructions stored in the storage 150 via the network 120. In some embodiments, the storage 150 may be directly connected to or communicate with one or more other components of the medical system 100 (e.g., the processing device 140, the terminal 130). In some embodiments, the storage 150 may be part of the processing device 140.

Figure 2:
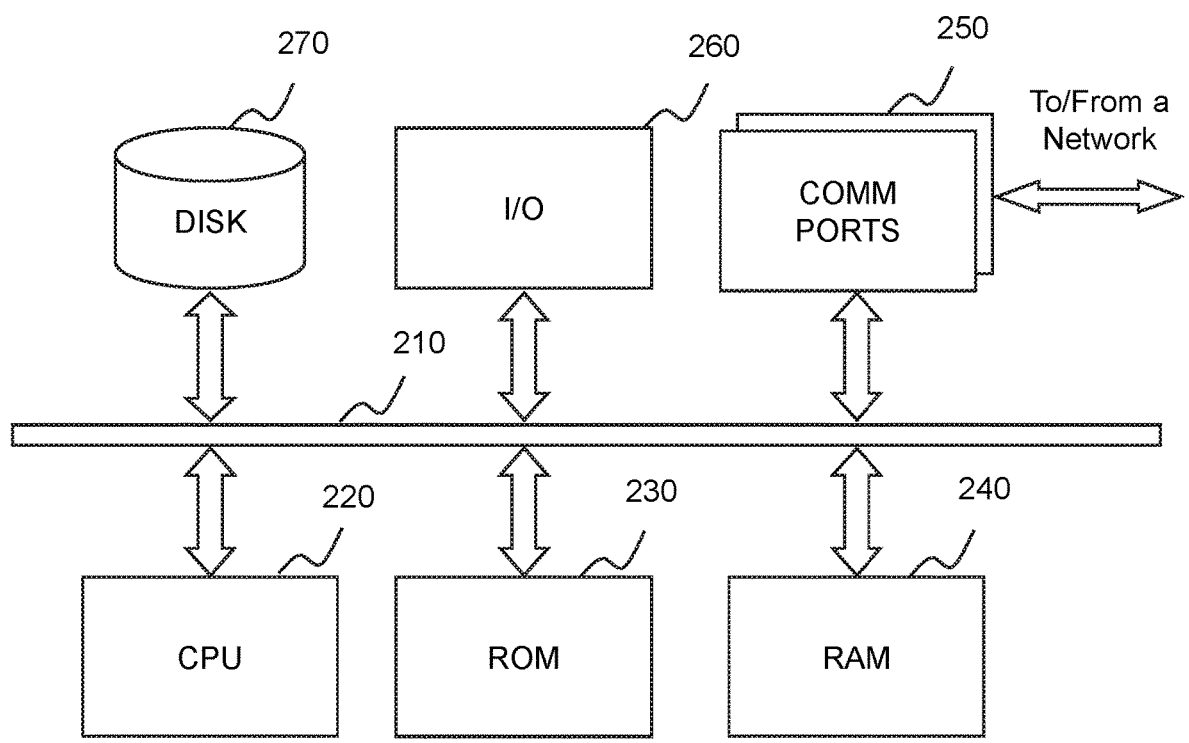
FIG. 2 is a schematic diagram illustrating an exemplary computing device on which the system can be implemented, according to some embodiments of the present disclosure.

FIG. 2 is a schematic diagram illustrating an exemplary computing device 200 on which the medical system 100 can be implemented, according to some embodiments of the present disclosure.

The computing device 200 may be a general purpose computer or a special purpose computer. Both may be used to implement a medical system of the present disclosure. The computing device 200 may be used to implement any component of the device as described herein. For example, the processing device 140 of the medical system 100 may be implemented on the computing device 200, via its hardware, software program, firmware, or a combination thereof. Although only one such computer is shown for convenience, the computer functions related to the medical system 100 as described herein may be implemented in a distributed manner on a number of similar platforms to distribute the processing load.

The computing device 200, for example, may include COMM ports 250 connected to and from a network (e.g., the network 120) connected thereto to facilitate data communications. The computing device 200 may also include a central processing unit (CPU) 220, in the form of one or more processors, for executing program instructions. The exemplary computer platform may include an internal communication bus 210, program storage and data storage of different forms, for example, a disk 270, and a read only memory (ROM) 230, or a random access memory (RAM) 240, for various data files to be processed and/or transmitted by the computer. The exemplary computer platform may also include program instructions stored in the ROM 230, the RAM 240, and/or other type of non-transitory storage medium to be executed by the CPU 220. The methods and/or processes of the present disclosure may be implemented as the program instructions. The computing device 200 also includes an I/O 260, supporting input/output between the computer and other components therein. The computing device 200 may also receive programming and data via network communications.

Merely for illustration, only one CPU and/or processor is described in the computing device 200. However, it should be noted that the computing device 200 in the present disclosure may also include multiple CPUs and/or processors, thus operations and/or method steps that are performed by one CPU and/or processor as described in the present disclosure may also be jointly or separately performed by the multiple CPUs and/or processors. For example, the CPU and/or processor of the computing device 200 executes both step A and step B. As in another example, step A and step B may also be performed by two different CPUs and/or processors jointly or separately in the computing device 200 (e.g., the first processor executes step A, and the second processor executes step B; or the first and second processors jointly execute steps A and B).

Figure 3:
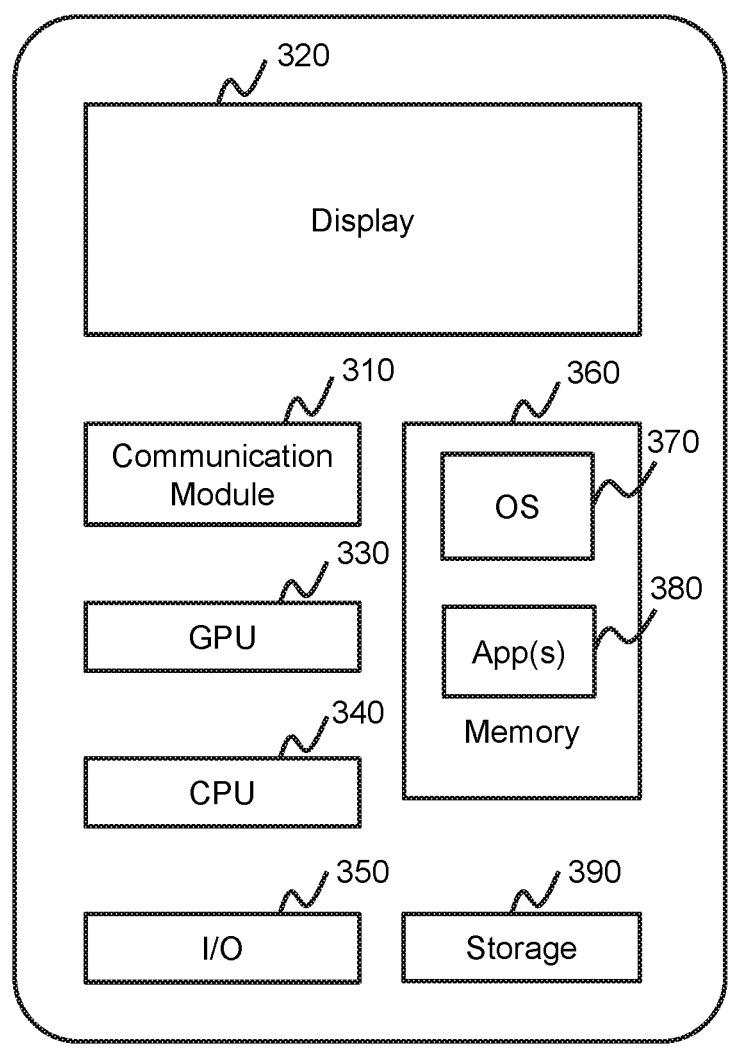
FIG. 3 is a schematic diagram illustrating exemplary hardware and/or software components of an exemplary mobile device on which the terminal may be implemented according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication module 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the medical system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
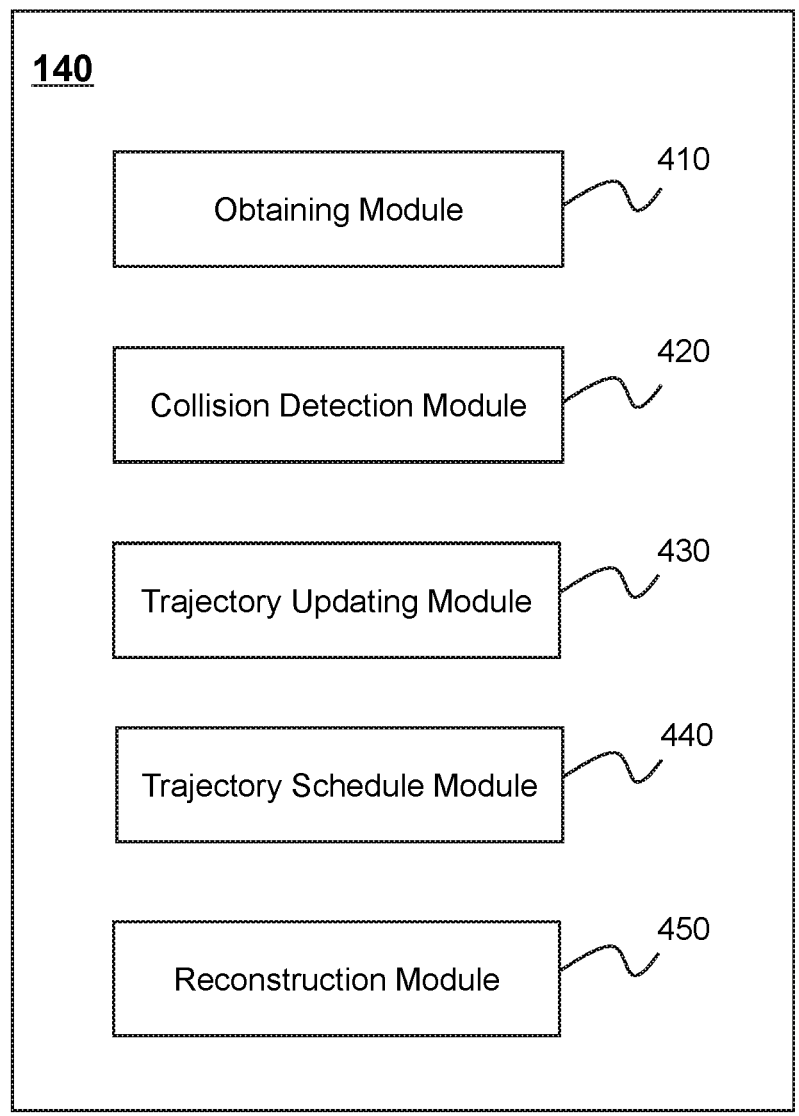
FIG. 4 is a block diagram illustrating an exemplary processing device according to some embodiments of the present disclosure.

FIG. 4 is a block diagram illustrating an exemplary processing device 140 according to some embodiments of the present disclosure. The processing device 140 may include an obtaining module 410, a collision detection module 420, a trajectory updating module 430, a trajectory schedule module 440 and a reconstruction module 450. The processing device 140 may be implemented on various components (e.g., the CPU 220 of the computing device 200 illustrated in FIG. 2).

The obtaining module 410 may obtain an initial trajectory of a component. In some embodiments, the initial trajectory may be obtained based on an initial geometry of the medical device 110. In some embodiments, the initial trajectory may be selected from a plurality of existing trajectories. The plurality of existing trajectories may be determined according to a machine-learning technique. Alternatively, the plurality of existing trajectories may be a collection of trajectories moved by the component before (e.g., in the previous 30 days). In some embodiments, the initial trajectory may be a default trajectory of the component of the medical device 110.

The collision detection module 420 may determine whether a collision is likely to occur. The collision may be likely to occur between different objects. For example, for a CBCT device, the collision may be likely to occur between a component of the CBCT device (e.g., the scanning source, the detector) and a subject (e.g., a patient, the table, the ground, the ceiling). For an RT device, the collision may be likely to occur between a component of the RT device (e.g., the irradiation head, the EPID) and a subject (e.g., a patient, the table, the ground, the ceiling). For a CBCT-RT device, the collision may be likely to occur between a component of the CBCT-RT device (e.g., the scanning source, the detector, the EPID, or the irradiation head) and a subject (e.g., a patient, the table, the ground, the ceiling). In some embodiments, the collision detection module 420 may perform the collision detection using dynamic collision detection techniques (e.g., hierarchical bounding volumes technique, space decomposition technique), one or more proximity transducers, or the like, or a combination thereof.

The trajectory updating module 430 may update the initial trajectory of the component and determine an updated trajectory. In some embodiments, the trajectory updating module 430 may update the initial trajectory using a machine-learning technique. In some embodiments, the trajectory updating module 430 may update the initial trajectory by increasing a distance between a component and a subject (e.g., a patient, a table). In some embodiments, the trajectory updating module 430 may update the initial trajectory by updating an initial orientation of the component on an initial position.

The trajectory schedule module 440 may determine one or more parameters associated with the initial (or updated) trajectory of the component. The initial (or updated) trajectory of the component may include a plurality of specific positions. The one or more parameters may ensure that the component may move from one specific position to a next specific position. The trajectory schedule module 440 may determine the one or more parameters associated with the specific positions. Specifically, the parameters may include a velocity, an accelerated velocity and/or a moving direction.

The reconstruction module 450 may reconstruct an image based on image data. The image data may be obtained according to the initial and/or updated trajectory. In some embodiments, the reconstruction module 450 may perform scale transformation and generate a plurality of virtual projection images based on the scale transformation. In some embodiments, the reconstruction module 450 may reconstruct an image according to the plurality of virtual projection images.

In some embodiments, one or more modules illustrated in FIG. 4 may be implemented in at least part of the exemplary system as illustrated in FIGS. 1A and 1B. For example, the collision detection module 420, the trajectory updating module 430, and the trajectory schedule module 440 may be integrated into a console (not shown). Via the console, a user may determine whether a collision is likely to occur, update a trajectory of a component if the collision is likely to occur, determine one or more parameters according to the updated trajectory of the component, etc. In some embodiments, the console may be implemented via the processing device 140 and/or the terminal 130.

Figure 5:
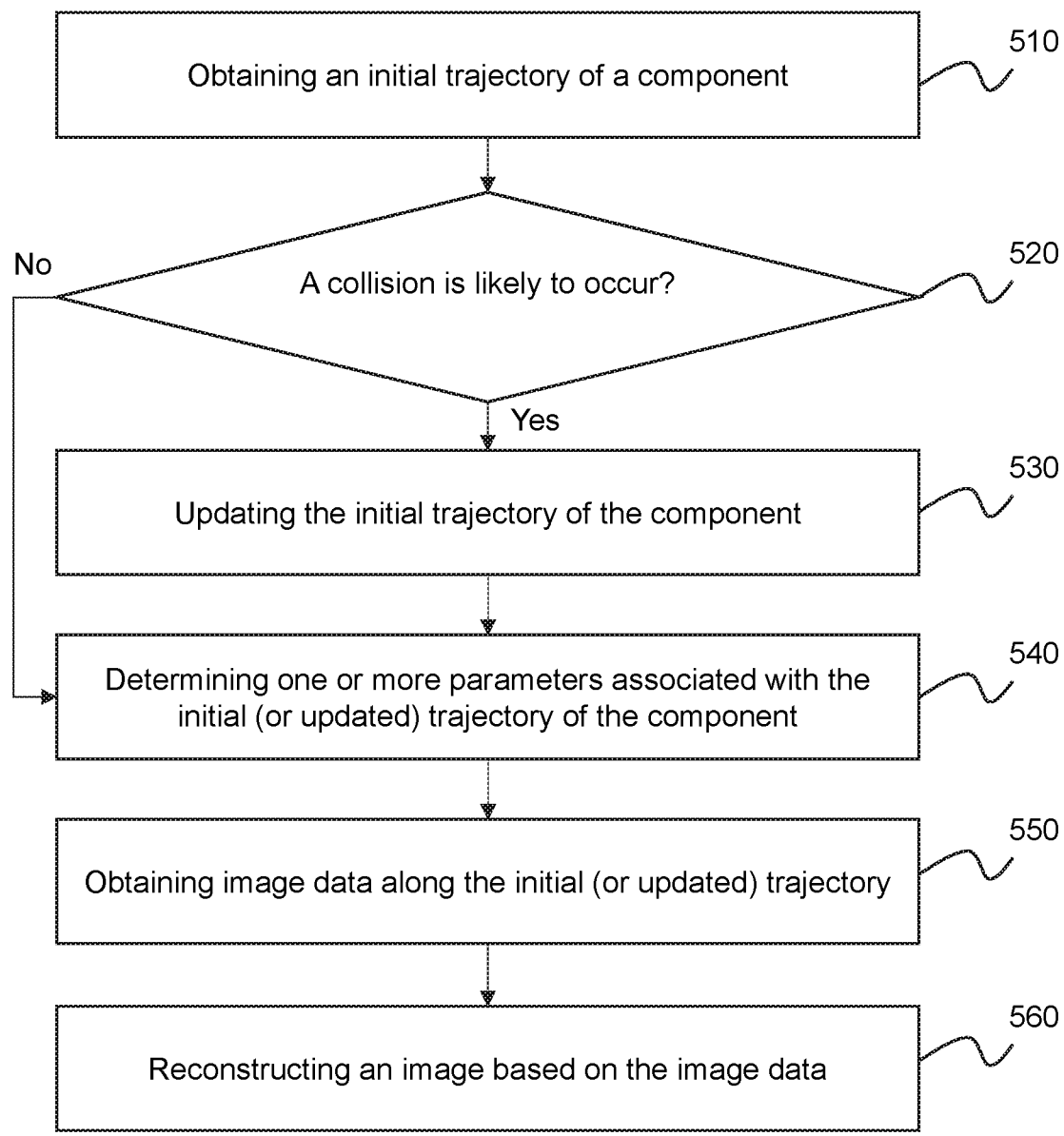
FIG. 5 is a flowchart illustrating an exemplary process for reconstructing an image according to some embodiments of the present disclosure.

FIG. 5 is a flowchart illustrating an exemplary process 500 for adjusting a geometry of a medical device according to some embodiments of the present disclosure. In some embodiments, process 500 may be performed by or be implemented on the processing device 140 of the medical system 100.

In 510, the obtaining module 410 may obtain an initial trajectory of a component. If the medical device is a CBCT device, the component may include a detector (e.g., the detector 112), and/or a scanning source (e.g., the scanning source 115). The scanning source 115 may be an X-ray source. If the medical device is an RT device, the component may include an irradiation head (e.g., the irradiation head 118), and/or an electronic portal imaging device (EPID) (e.g., EPID 119). If the medical device is a CBCT-RT device, the component may include a detector (e.g., the detector 123), a scanning source (e.g., the scanning source 124), an irradiation head (e.g., the irradiation head 122), and/or an EPID (e.g., EPID 125). The initial trajectory may be obtained based on an initial geometry of the medical device 110. For example, the initial trajectory may be a default trajectory of the component in the initial geometry. The initial geometry may be determined according to the initial settings of the medical device 110. As another example, the initial trajectory may be a historical trajectory (e.g., a trajectory used in the last time), which may be the same as or different from the default trajectory.

Figure 7A:
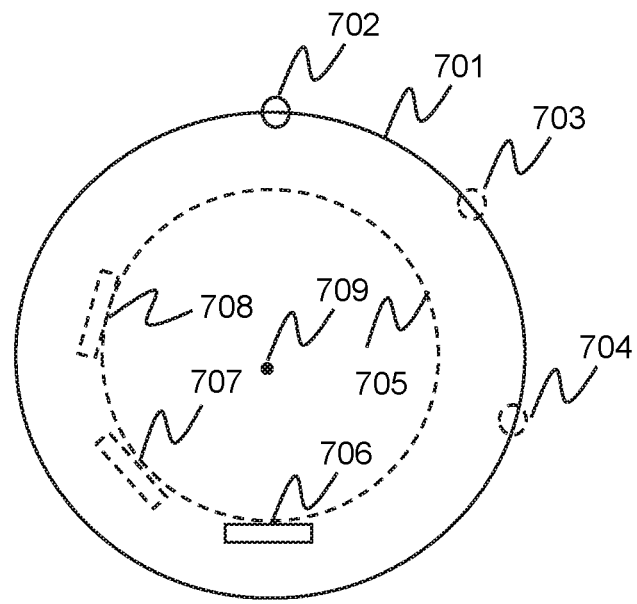
FIG. 7A illustrates an exemplary initial geometry of a CBCT according to some embodiments of the present disclosure.
Figure 7B:
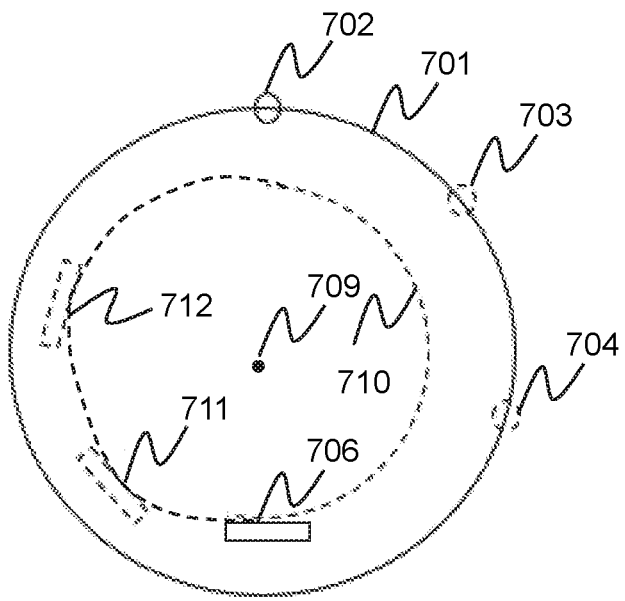
FIG. 7B illustrates an exemplary updated geometry of a CBCT according to some embodiments of the present disclosure.

In some embodiments, the initial trajectory may be a circle, half circle, any type of incomplete circle, or other shape of curves. Merely by way of example, FIG. 7A shows an initial trajectory 705 of the detector 112 and an initial trajectory 701 of the scanning source 115 of a CBCT device. The initial trajectory 701 of the scanning source 115 may be a circle. The initial trajectory 705 of the detector 112 may also be a circle. In some embodiments, the initial trajectory of a component (e.g., the scanning source 115, the detector 112) may include a plurality of initial positions of the component. The plurality of initial positions may be distributed on the initial trajectory evenly or unevenly. For example, the initial trajectory 701 in FIG. 7A may include a plurality of initial positions of the scanning source 115, for example, a first initial position 702, a second initial position 703, a third initial position 704. The plurality of initial positions of the scanning source 115 may be distributed on the initial trajectory 701 evenly. As another example, the initial trajectory 705 in FIG. 7A may include a plurality of initial positions of the detector 112, for example, a first initial position 706, a second initial position 707, a third initial position 708. The plurality of initial positions of the detector 112 may be distributed on the initial trajectory 705 evenly. Each initial position of the detector 112 may correspond to one initial position of the scanning source 115. For example, the first initial position 706 may correspond to the first initial position 702. As another example, the second initial position 707 may correspond to the second initial position 703. As still another example, the third initial position 708 may correspond to the third initial position 704. In FIG. 7A, an initial position of the scanning source 115, a corresponding initial position of the detector 112, and the isocenter 709 may be aligned in a straight line. For illustration purposes only, assume that the detector 112 is unlikely to collide with the patient or the table 114 in the first initial position 706, but the detector 112 is likely to collide with the patient or the table 114 in the second initial position 707 and the third initial position 708. When the collision detection module 420 determines that a collision is likely to occur between the detector 112 and the patient or the table 114 in the second initial position 707 or the third initial position 708, the trajectory updating module 430 may update the trajectory of the detector 112 such that the collision will be avoided. For example, the trajectory updating module 430 may increase (or cause the medical device 100 to increase) the distance between the detector 112 and the isocenter 709 (or the distance between the detector 112 and the patient or the table 114) shown in FIG. 7B. Accordingly, as shown in FIG. 7B, the detector 112 may move from the second initial position 707 to the position 711 (an updated position) to avoid the collision and from the third initial position 708 to the position 712 (an updated position).

In some embodiments, the component may rotate a circle to scan and/or treat a target subject to be examined. In some embodiments, the component in each of the initial positions may have an initial orientation relative to a tangent of the initial trajectory at the corresponding initial position. The initial orientation may be in a range from 0 degree to 90 degrees.

In 520, the collision detection module 420 may determine whether a collision is likely to occur. The collision may be likely to occur between different objects, for example, between a component (e.g., the scanning source, the detector, the irradiation head, the EPID) and a subject (e.g., a patient, the table, the ground, the ceiling). For example, for the CBCT device 110-1, the collision may be likely to occur between the patient and the detector 112, between the patient and the scanning source 115, between the scanning source 115 and the table 114, and/or between the detector 112 and the table 114. As another example, for the RT device 110-2, the collision may be likely to occur between the patient and the irradiation head 118, between the patient and the EPID 119, between the table 117 and the EPID 119, and/or between the table 117 and the irradiation head 118. As still another example, for the CBCT-RT device 110-3, the collision may be likely to occur in one or more situations as mentioned in the CBCT device 110-1 and the RT device 110-2.

An irradiation head may include an MLC inside or outside the shell of the irradiation head. If the MLC is inside the shell (e.g., as illustrated in FIGS. 9B through 9D), the collision may be likely to occur between the subject (e.g., the patient, the table) and the shell. Alternatively, if the MLC is outside the irradiation head (e.g., as illustrated in FIG. 9A), the collision may be likely to occur between the subject (e.g., the patient, the table) and the MLC.

In some embodiments, the collision detection may occur during the scanning and/or treatment of a target subject. For example, for a CBCT device (e.g., the CBCT device 110-1), when the CBCT device is scanning the target subject to determine an image of the target subject, the collision detection module 420 may determine whether a collision is likely to occur between the component (e.g., the scanning source 115, the detector 112) of the CBCT device and a subject (e.g., a patient, the table 114, the ground, the ceiling) in each of positions of the trajectory of the component during the movement of the component. If the collision detection module 420 determines that a collision is likely to occur between the component and the subject, the trajectory updating module 430 may update the trajectory of the component of the CBCT device in real time. For a radiotherapy (RT) device (e.g., the RT device 110-2), when the RT device is treating the target subject, the collision detection module 420 may determine whether a collision is likely to occur between the component (e.g., the irradiation head 118, the EPID 119) of the RT device and a subject (e.g., a patient, the table 117, the ground, the ceiling) in each of positions of the trajectory of the component during the movement of the component. If the collision detection module 420 determines that a collision is likely to occur between the component and the subject, the trajectory updating module 430 may update the trajectory of the component of the RT device in real time. For a CBCT-RT device (e.g., the CBCT-RT device 110-3), during the CBCT-RT device scans and/or treats the target subject, the collision detection module 420 may determine whether a collision is likely to occur between the component (e.g., the irradiation head 122, the detector 123, the scanning source 124, the EPID 125) of the CBCT-RT device and a subject (e.g., a patient, the table 121, the ground, the ceiling). If the collision detection module 420 determines that a collision is likely to occur between the component and the subject, the trajectory updating module 430 may update the trajectory of the component of the CBCT-RT device to avoid the collision during the movement of the component of the CBCT-RT device.

In some embodiments, the collision detection may occur before the scanning and/or treatment of the target subject. For example, for a CBCT device (e.g., the CBCT device 110-1), before the CBCT device scans the target subject, the collision detection module 420 may determine whether a collision is likely to occur between the component (e.g., the scanning source 115, the detector 112) and a subject (e.g., a patient, the table 114, the ground, the ceiling). If the collision detection module 420 determines that a collision is likely to occur between the component and a subject, the trajectory updating module 430 may update the trajectory of the component of the CBCT to avoid the collision before the CBCT device scans the target subject. When the CBCT device begins to scan the target subject, the component of the CBCT device that is likely to collide with the subject may move along an updated trajectory to obtain image data to determine the image of the target subject. For an RT device (e.g., the RT device 110-2), before the RT device treats the target subject, the collision detection module 420 may determine whether a collision is likely to occur between the component (e.g., the irradiation head 118, the EPID 119) of the RT device and a subject (e.g., a patient, the table 117, the ground, the ceiling). If the collision detection module 420 determines that a collision is likely to occur between the component and a subject, the trajectory updating module 430 may update the trajectory of the component of the RT device to avoid the collision before the RT device treats the target subject. When the RT device begins to treat the target subject, the component of the RT device that is likely to collide with the subject may move along an updated trajectory to treat the target subject. For a CBCT-RT device (e.g., the CBCT-RT device 110-3), before the CBCT-RT device scans and/or treats the target subject, the collision detection module 420 may determine whether a collision is likely to occur between the component (e.g., the irradiation head 122, the detector 123, the scanning source 124, the EPID 125) of the CBCT-RT device and a subject (e.g., a patient, the table 121, the ground, the ceiling). If the collision detection module 420 determines that a collision is likely to occur between the component and a subject, the trajectory updating module 430 may update the trajectory of the component of the CBCT-RT device to avoid the collision before the CBCT-RT device scans and/or treat the target subject. When the CBCT-RT device begins to scan and/or treat the target subject, the component of the CBCT-RT device that is likely to collide with the subject may move along an updated trajectory to detect and/or treat the target subject.

In some embodiments, the collision detection may occur after the scanning and/or treatment of a target subject. For example, after the scanning and/or treatment of a first target subject, the collision detection module 420 may determine whether a collision is likely to occur between a component of the medical device (e.g., a CBCT device, an RT device, or a CBCT-RT device) and a subject (e.g., a second target subject, the table, the ground, the ceiling). The collision detection module 420 may obtain one or more features of the subject (e.g., a gender, height, a girth, a size, etc) and a target region of the subject. Further, the collision detection module 420 may determine whether a collision is likely to occur between the component of the medical device and the subject based on the one or more features and the target region.

In some embodiments, the collision detection module 420 may perform the collision detection using a dynamic collision detection technique, including, for example, a hierarchical bounding volumes technique or space decomposition technique. The collision detection module 420 may use the dynamic collision detection technique during scanning and/or treating a target subject, before scanning and/or treating the target subject, or after scanning and/or treating the target subject. For instance, the collision detection module 420 may determine whether a collision is likely to occur using the hierarchical bounding volumes technique. The collision detection module 420 may determine a volume and/or position of an object (e.g., the scanning source, the table, the detector, the irradiation head, the patient, the ground, the ceiling.) The collision detection module 420 may then assign a corresponding bounding box to the object according to the volume and/or position of the object. The bounding box may be with a regular shape (e.g., a rectangular cuboid, sphere, cylinder, ellipsoid) or an irregular shape. The collision detection module 420 may further determine whether a collision is likely to occur between the bounding boxes. In response to determining a collision is likely to occur between the bounding boxes, the collision detection module 420 may determine a collision is likely to occur between the different objects. On the other hand, in response to determining a collision is not likely to occur between the bounding boxes, the collision detection module 420 may determine a collision is not likely to occur between the different objects, and the component may move according to the initial trajectory through the initial positions. Descriptions regarding the hierarchical bounding volumes technique may be found in, for example, James T. et al., Transactions on Visualization and Computer Graphics, 4 (1): 21-36 (1998), which is hereby incorporated by reference.

In some embodiments, the collision detection may be performed based on one or more proximity transducers. The one or more proximity transducers may detect signals relating to positions of components and send the signals to the collision detection module 420. The collision detection module 420 may determine whether a collision is likely to occur according to the signals during scanning and/or treating a target subject, before scanning and/or treating the target subject, or after scanning and/or treating the target subject. The proximity transducers may be mounted on the objects, including the component (e.g., the scanning source, the detector, the irradiation head, the EPID) and/or the subject (e.g., a patient, the table, the ground, the ceiling). The one or more proximity transducers may detect a distance between different objects, for example, between the component (e.g., the scanning source, the detector, the irradiation head, the EPID) of a medical device (e.g., the CBCT device 110-1, the RT device 110-2, the CBCT-RT device 110-3) and the subject (e.g., a patient, the table, the ground, the ceiling). The proximity transducers may include a capacitive proximity transducer, an Eddy-current proximity transducer, a Hall Effect proximity transducer, a Doppler Effect proximity transducer, etc.

The collision detection module 420 may determine whether a collision is likely to occur between two objects according to the distance between the two objects and a threshold. The collision detection module 420 may compare the distance with the threshold. If the collision detection module 420 determines that the distance is less than the threshold, the collision detection module 420 may determine that a collision is likely to occur between the two objects. Process 500 may proceed to 530 to update the initial trajectory of the component. On the other hand, if the collision detection module 420 determines that the distance is not less than the threshold, the collision detection module 420 may determine that a collision is not likely to occur between the two objects, and process 500 may proceed to step 540 directly to perform trajectory planning. The threshold may include a default value, a value set automatically by, for example, the collision detection module 420, or a value set manually by a user, or a value adaptively adjusted by the medical system 100. The threshold may be any suitable value between 0 to 20.0 centimeters. In some embodiments, the threshold may be from 0 to 10.0 centimeters or 10.1 centimeters to 20.0 centimeters. In some embodiments, the threshold may be from 0 to 5 centimeters or from 5 centimeters to 10 centimeters. In some embodiments, the threshold may be 1 centimeter, 2 centimeters, 3 centimeters, 4 centimeters, etc.

In 530, the trajectory updating module 430 may update the initial trajectory of the component and determine an updated trajectory. For illustration purposes, FIG. 7B shows an updated trajectory 710 of the detector 112. The updated trajectory 710 may include a plurality of updated positions of the detector 112, for example, an updated position 711, an updated position 712. In some embodiments, the trajectory updating module 430 may update the initial trajectory using a machine-learning technique. For example, the trajectory updating module 430 may generate a plurality of trajectories of the component based on the machine-learning technique. The trajectory updating module 430 may further obtain one or more features of an object (e.g., a component, a subject) and select one of the plurality of trajectories as the updated trajectory based on the one or more features of the object. As another example, the trajectory updating module 430 may access a plurality of existing trajectories of the component (e.g., historical trajectories of the component) stored in a storage device (e.g., the storage 150), each trajectory corresponding to one or more features of an object (e.g., a component, a subject). The trajectory updating module 430 may select one of the plurality of trajectories as the updated trajectory using the machine-learning technique according to the one or more features of the target subject. As for the object being a patient, the one or more features may include a gender, height, a girth, a size, etc.

In some embodiments, the trajectory updating module 430 may update the initial trajectory by increasing a distance between a subject (e.g., a patient, a table) and the component that is likely to collide with the subject. For example, during a CBCT scanning, the trajectory updating module 430 may increase a distance between the detector 112 and the patient or the table 114, and/or between the scanning source 115 and the patient or the table 114. For illustration purposes, the updated trajectory 710 shown in FIG. 7B may be generated by increasing a distance between the detector 112 and the isocenter 709, for example, by adjusting the second initial position 707 to the updated position 711, adjusting the initial third position 708 to the updated position 712. As another example, during radiotherapy by an RT device, the trajectory updating module 430 may increase a distance between the irradiation head 118 and the patient (or the table 117), or between the EPID 119 and the patient (or the table 117).

The trajectory updating module 430 may increase the distance between the component and the subject by updating an initial position of the component in the initial trajectory of the component. For example, for a CBCT device, the trajectory updating module 430 may update the initial position of the component (e.g., the detector 112 and/or the scanning source 115) of the CBCT device that is likely to collide with the subject. The updating of the component of the CBCT device may be along a straight line defined by the scanning source 115, the isocenter and the detector 112 (the radial direction), along the tangent of the initial trajectory of the detector 112 and/or the scanning source 115, along a horizontal direction, along a vertical direction, or the like, or a combination thereof. As another example, for an RT device, the trajectory updating module 430 may update the initial position(s) of the component (e.g., the irradiation head 118 and/or the EPID 119) of the RT device that is likely to collide with the subject. The updating of the initial position of the component of the RT device may be along the straight line defined by the EPID 119, the isocenter, and the irradiation head 118 (the radial direction), along the tangent of the initial trajectory of the irradiation head and/or the EPID, along the horizontal direction, along the vertical direction, or the like, or a combination thereof. For a CBCT-RT device, the trajectory updating module 430 may update the initial position(s) of the component (e.g., the irradiation head 122, the detector 123, the scanning source 124, the EPID 125) of the CBCT-RT device that is likely to collide with the subject. The updating of the initial position of the component of the CBCT-RT device may be along the radial direction, along the tangent of the initial trajectory of the component, along the horizontal direction, along the vertical direction, or the like, or a combination thereof. The horizontal direction may be a direction parallel to the ground. The vertical direction may be a direction perpendicular to the ground.

Alternatively or additionally, the trajectory updating module 430 may also update the initial trajectory by updating an initial orientation of the component relative to a tangent on an initial position. For example, for a CBCT device, the trajectory updating module 430 may adjust an orientation of the component (e.g., the detector 112 and/or the scanning source 115) of the CBCT device that is likely to collide with the subject. As another example, for an RT device, the trajectory updating module 430 may adjust an orientation of the component (e.g., the irradiation head 118 and/or the EPID 119) of the RT device that is likely to collide with the subject. For instance, for an RT device, if the collision may be likely to occur between the EPID 119 and the table 117, the trajectory updating module 430 may update the initial trajectory of the EPID 119. The trajectory updating module 430 may increase the distance between the EPID 119 and the table 117 firstly. If the collision is still likely to occur when the distance between the EPID 119 and the table 117 reaches a threshold value, the trajectory updating module 430 may adjust the orientation of the EPID. For a CBCT-RT device, the trajectory updating module 430 may adjust an orientation of the component (e.g., the irradiation head 122, the detector 123, the scanning source 124, the EPID 125) of the CBCT-RT device that is likely to collide with the subject. In some embodiments, the trajectory updating module 430 may update the initial trajectory by performing one or more operations as described in connection with FIG. 6.

In 540, the trajectory schedule module 440 may determine one or more parameters associated with an actual trajectory of the component. The actual trajectory may be the initial trajectory or the updated trajectory. Alternatively, the actual trajectory may be a combination of part of the initial trajectory and part of the updated trajectory if the component initially moves along the initial trajectory, but later is adjusted to move along an updated trajectory to avoid a possible collision determined by the collision detection module 420.

In some embodiments, if the collision detection module 420 determines that the collision is not likely to occur, the actual trajectory may be the initial trajectory, and the trajectory schedule module 440 may use initial parameters associated with the initial trajectory, or re-determine the one or more parameters associated with the initial trajectory of the component. If the collision detection module 420 determines that the collision is likely to occur, the actual trajectory may be the updated trajectory, and the trajectory schedule module 440 may determine the one or more parameters associated with the updated trajectory of the component. The determined one or more parameters may include a velocity, a moving direction, an accelerated velocity, etc., associated with the plurality of positions of the actual trajectory of the component.

In some embodiments, process 500 may further include step 550 and step 560. In 550, the obtaining module 410 may obtain image data along the actual trajectory (the initial trajectory or the updated trajectory). The obtaining module 410 may obtain the actual trajectory of the component and obtain the image data of the scanning according to the actual trajectory. In the motion of the component along the actual trajectory, the scanning source 115 may emit a cone beam of rays (e.g., X-rays) to a subject to be examined (e.g., a patient or other subject to be examined). The detector 112 may detect attenuated rays (e.g., attenuated X-rays) passing through the subject. The attenuated rays may be converted to the image data of the scanning.

In 560, the reconstruction module 450 may reconstruct an image based on the image data. In some embodiments, the updated trajectory may be generated by updating the position of the detector 112 from an initial position to a corresponding updated position. As shown in FIGS. 7A and 7B, the detector 112 may move from the second position 707 (an initial position) to the position 711 (an updated position) to avoid the collision. When the detector 112 moves from an initial position to a corresponding updated position, the reconstruction module 450 may further determine a virtual projection image in the initial position corresponding to the updated position based on the image data and a scale transformation.

Figure 8:
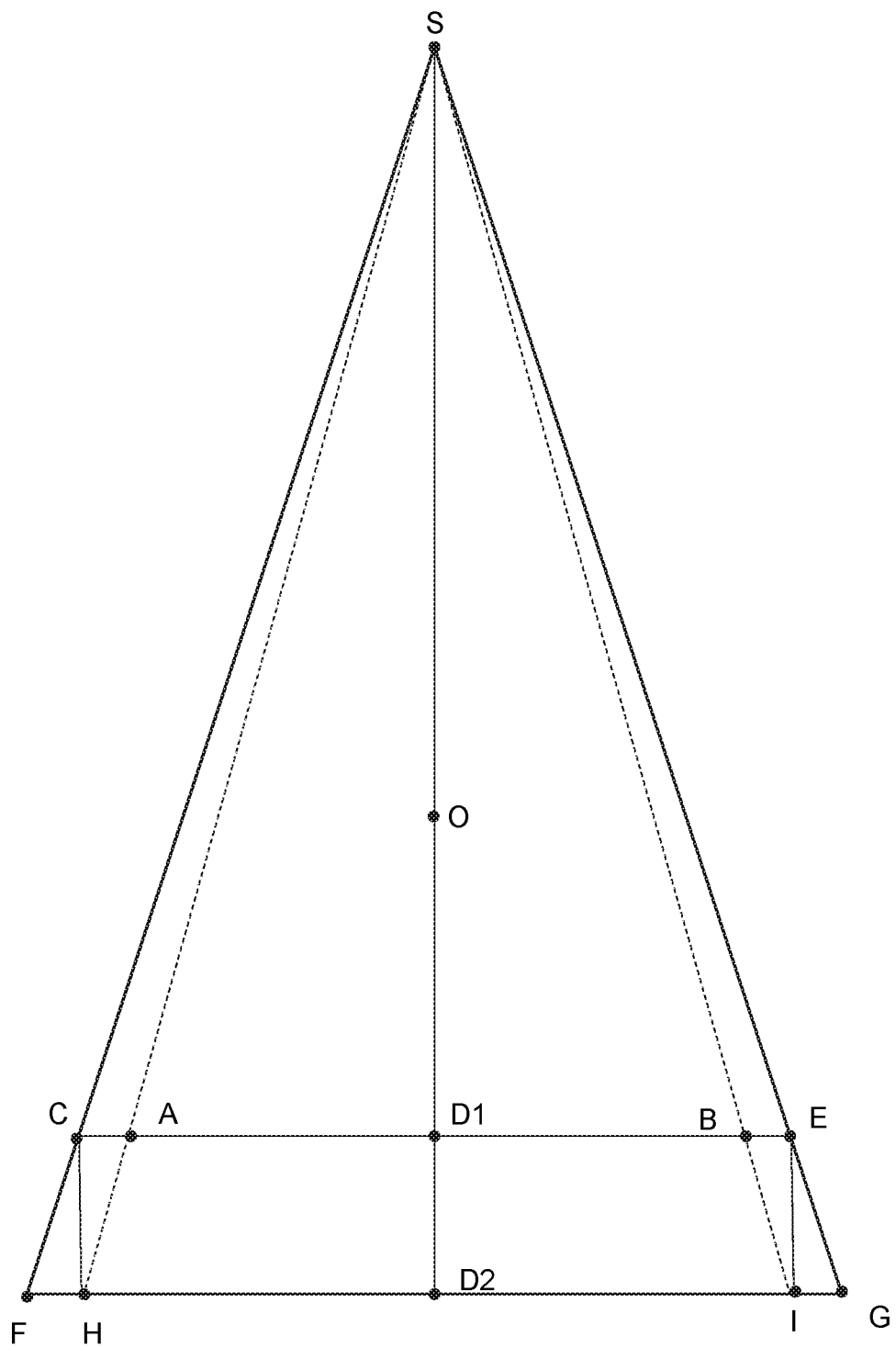
FIG. 8 illustrates an exemplary diagram of a CBCT according to some embodiments of the present disclosure.

FIG. 8 shows a diagram of a medical device according to some embodiments of the present disclosure. The medical device may include a CBCT device, an RT device, or a CBCT-RT device. For illustration purposes, take a CBCT device as an example. The point S represents the scanning source 115, and the point O represents an isocenter. The point D1 represents the position of the center of the detector 112 in an initial position, and the point D2 represents the position of the center of the detector 112 in an updated position. The line segment CE represents the detector 112 in the initial position (the length of CE represents the length of the detector 112). The line segment HI represents the detector 112 in the updated position (the length of HI represents the length of the detector 112). The line segment HI is parallel to the line segment CE. The isocenter refers to the center of rotation of the gantry 111 of the medical device 110, for example, the rotation of the scanning source 115, and the detector 112. In some embodiments, the center of a region of interest of a patient may be aligned with the isocenter. The region of interest of the patient refers to a region to be scanned. A geometry formed by a point S, point C, point A, point D1, point B, and point E is referred to herein as the geometry SCAD1BE (also referred to herein as an initial geometry). A geometry formed by a point S, point F, point H, point D2, point I, and point G is referred to herein as the geometry SFHD2IG (also referred to herein as an updated geometry).

In some embodiments, the isocenter, the scanning source 115, and the center of the detector 112 may be aligned in a straight line. In some embodiments, the isocenter, the scanning source 115, and the center of the detector 112 may be not in a straight line.

As shown in FIG. 8, the isocenter, the scanning source 115, and the center of the detector 112 are aligned in a straight line, and the line segment CE is parallel to the line segment FG. It should be noted that the description of the geometry is merely an example, and is not intended to be limiting.

When the position of the detector 112 is on the line segment CE (the length of CE represents the length of the detector 112), the detector 112 may detect attenuated rays corresponding to the line segment CE. After the position of the detector 112 is updated from the line segment CE to the line segment HI, the attenuated rays received by the detector 112 are limited by the shape S-H-I. Thus, when generating a virtual projection image on the initial position (i.e., line segment CE), the detector 112 may provide ray-information corresponding to the line segment AB and may not provide ray-information corresponding to the line segments CA and BE. Accordingly, the virtual projection image on the initial position may be scaled. For example, if the length of SD1 is a first value, L1, e.g., 140 cm, the length of SD2 is a second value, L2, e.g., 145 cm, the length of the detector 112 (i.e., the length of CE and/or HI) is a third value L3, e.g., 40 cm, the virtual projection image may be scaled as L3*L1/L2, e.g., 40*140/145.

In some embodiments, the reconstruction module 450 may interpolate ray-information corresponding to the line segments CA and BE based on the ray-information corresponding to the line segment AB. The virtual projection image may be determined based on the ray-information corresponding to the line segment AB and the interpolated ray-information corresponding to the line segments CA and BE. In some embodiments, the reconstruction module 450 may reconstruct an image according to the plurality of virtual projection images obtained as described above. The reconstructed image may be a 3D image.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 6:
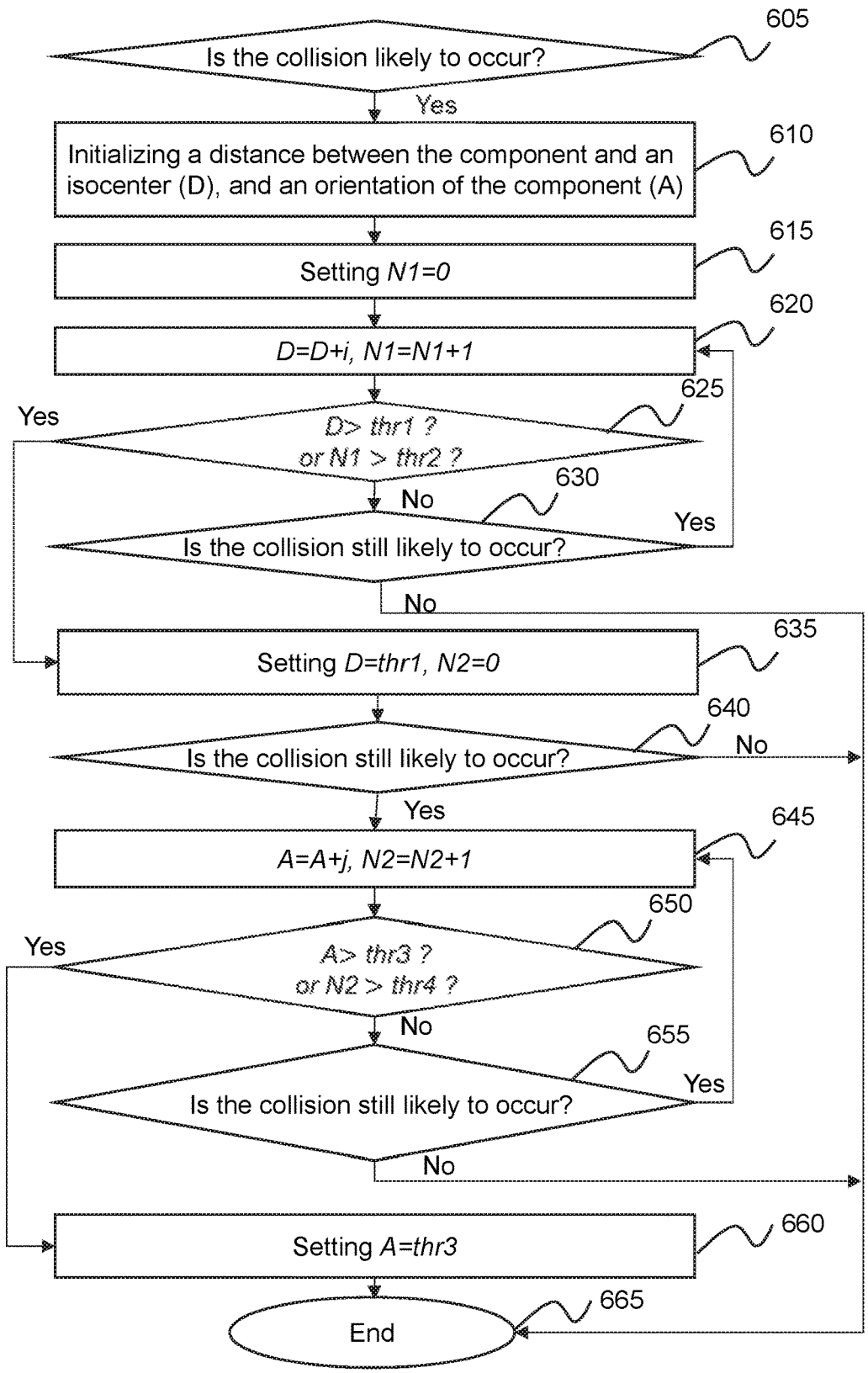
FIG. 6 is a flowchart illustrating an exemplary process for updating a trajectory of the component according to some embodiments of the present disclosure.

In some embodiments, step 520 and step 530 of the process 500 may be performed according to an exemplary process for updating a trajectory of a component of a medical device illustrated in FIG. 6. In some embodiments, process 600 may be performed by or be implemented on the processing device 140 of the medical system 100.

In 605, the collision detection module 420 may determine whether a collision between a component of the medical device 110 and a subject is likely to occur. If the collision detection module 420 determines that a collision is likely to occur between a component of the medical device 110 and a subject, process 600 may proceed to step 610. On the other hand, if the detection module 420 determines that a collision is unlikely to occur between a component of the medical device 110 and a subject, process 600 may end. The subject may include a patient, an organ, tissue, a phantom, a table, ground, a ceiling, etc. For the CBCT device 110-1, the component may include the detector 112, the scanning source 115, etc. For the RT device 110-2, the component may include an irradiation head 118, the EPID 119, etc. For a CBCT-RT device 110-3, the component may include the irradiation head 122, the detector 123, the scanning source 124, the EPID 125. The irradiation head 118 or the irradiation head 122 may include a shell 905, a target 901, a primary collimator 902, jaws 903, a multi-leaf collimator (MLC) 904. In some embodiments, the MLC 904 may be outside the irradiation head as illustrated in FIG. 9A. In some embodiments, the MLC 904 may be inside the irradiation head as illustrated in FIGS. 9B through 9D. When the MLC 904 is configured outside the irradiation head (i.e., configured outside the shell 905 of the irradiation head), the collision detection module 420 may determine whether the MLC 904 may collide with the subject (e.g., a patient or the table). When the MLC 904 is inside the irradiation head, the collision detection module 420 may determine whether the shell 905 of the irradiation head may collide with the subject (e.g., a patient or the table).

In some embodiments, the collision detection module 420 may determine whether a collision is likely to occur during imaging and/or treatment of the medical device 110, for example, during a movement of the component of the medical device 110. In some embodiments, the collision detection module 420 may determine whether a collision is likely to occur before imaging and/or treatment of the medical device 110. In some embodiments, the collision detection module 420 may determine whether a collision is likely to occur after imaging and/or treatment of the medical device 110.

In 610, the trajectory updating module 430 may initialize a distance between the component and an isocenter (e.g., the isocenter 709) and an orientation of the component. The distance may be marked as D, and the orientation may be marked as A.

In 615, the trajectory updating module 430 may set the iteration number for distance of the component, N1, as "0."

In 620, the trajectory updating module 430 may update the distance between the component and the isocenter 709. The distance between the component and the isocenter 709 may be updated by adding a distance increment (represented by i), i.e., D1=D1+i. The distance increment may be set automatically by, for example, the trajectory updating module 430 or manually by a user. The value of the distance increment may be any suitable value from 0 to 5.0 centimeters or larger than 5.0 centimeters. In some embodiments, the value of the distance increment may be a value from 0.1 centimeters to 1.0 centimeter, from 1.1 centimeters to 2.0 centimeters, from 2.1 centimeters to 3.0 centimeters, 3.1 centimeters to 4.0 centimeters, 4.1 centimeters to 5.0 centimeters Accordingly, the iteration number for distance, N1, may be updated by adding "1," i.e., N1=N1+1.

In some embodiments, the trajectory updating module 430 may update the distance by updating an initial position of the component in the initial trajectory of the component. For the CBCT device, the trajectory updating module 430 may update an initial position of the detector 112 and/or the scanning source 115 along any direction, for example, along a straight line defined by the scanning source 115, the isocenter and the detector 112 (the radial direction), along the tangent of the initial trajectory of the detector 112 and/or scanning source 115, and/or along a horizontal direction or a vertical direction.

For the RT device, the trajectory updating module 430 may update an initial position of the irradiation head and/or the EPID in the corresponding initial trajectory of the irradiation head and/or the EPID. For the CBCT-RT device, the trajectory updating module 430 may update an initial position of the scanning source, the detector, the irradiation head, and/or the EPID in the corresponding initial trajectory of the component. For the RT device and/or the CBCT-RT device, the irradiation head of device may include an MLC. In some embodiments, the MLC 904 may be configured outside the shell 905 of an irradiation head (e.g., the irradiation head 118, the irradiation head 122), as illustrated in FIG. 9A. In FIG. 9A, the target 901, the primary collimator 902, and the jaws 903 are configured inside the shell 905, while the MLC 904 is configured outside the shell 905. Referring to the left side of FIG. 9A, if a collision is likely to occur between a subject and the irradiation head, the collision may be likely to occur between the subject and the MLC 904. Accordingly, the trajectory updating module 430 may update an initial position of the MLC 904 in the initial trajectory of the MLC 904. Referring to FIG. 9A, compared the left side of FIG. 9A with the right side of FIG. 9A, only the position of the MLC 904 is updated, while the positions of the shell 905 and the components within the shell 905 may be maintained. In some embodiments, when the MLC is outside the shell, both the shell and the MLC may be likely to collide with a subject, therefore, the position of the MLC and the position of the shell may need to be updated to avoid the collision.

In some embodiments, the MLC 904 may be configured inside the shell 905 of the irradiation head (e.g., the irradiation head 118, the irradiation head 122), as illustrated in FIGS. 9B through 9D. In FIGS. 9B through 9D, the target 901, the primary collimator 902, the jaws 903, and the MLC 904 are configured inside the shell 905.

If a collision is likely to occur between a subject and the irradiation head, the collision may be likely to occur between the subject and the shell 905. Accordingly, the trajectory updating module 430 may update an initial position of the shell 905, while the positions of the components within the shell 905 (e.g., the target 901, the primary collimator 902, the jaws 903, the MLC 904) may be or not be updated. For example, when the space between the shell 905 and the MLC is large enough to avoid the collision between the shell 905 and the subject, the trajectory updating module 430 may merely update an initial position of the shell 905 in the initial trajectory of the shell 905 and may not update positions of the components within the shell 905 (e.g., the target 901, the primary collimator 902, the jaws 903, and the MLC 904), as shown in FIG. 9B. As another example, the trajectory updating module 430 may update an initial position of the shell 905 in the initial trajectory of the shell 905, and also update at least one position of the components within the shell 905 (e.g., the target 901, the primary collimator 902, the jaws 903, or the MLC 904). For instance, referring to FIG. 9C, the position of the target 901 remains unchanged, and the trajectory updating module 430 may update an initial position of the shell 905, the primary collimator 902, the jaws 903, and the MLC 904 in the corresponding initial trajectory of the shell 905, the primary collimator 902, the jaws 903, and the MLC 904. The relative positions between any two of the primary collimator 902, the jaws 903, and the MLC 904 may be or not be changed. FIG. 9C shows the updating of positions of the shell 905, the primary collimator 902, the jaws 903, and the MLC 904. It should be noted that it is merely an example, and is not intended to be limiting. In some embodiments, the trajectory updating module 430 may only update the positions of the shell 905 and the MLC 904. In some embodiments, the trajectory updating module 430 may only update the positions of the shell 905, the MLC 904, and the jaws 903.

In some embodiments, the trajectory updating module 430 may update an initial position of the shell 905, the target 901, the primary collimator 902, the jaws 903, and the MLC 904, as shown in FIG. 9D. The relative positions between the target 901, the primary collimator 902, the jaws 903, and the MLC 904 may be or not be changed. It should be noted that, if the position of the primary collimator 902, the jaws 903, or the MLC 904 changes (as illustrated in FIGS. 9C and 9D), the aperture defined by the primary collimator 902, the jaws 903, or the MLC 904 may also be accordingly and proportionally changed to make a treatment plan implemented as the former. For example, the trajectory updating module 430 may change a beam field defined by the MLC 904.

In 625, the trajectory updating module 430 may determine whether the updated distance is greater than a first threshold (represented by thr1). The first threshold, thr1, may be determined based on the farthest position of the component away from the isocenter that the component can achieve. In some embodiments, the farthest position of the component away from the isocenter may be determined according to the physical construction of the component. In some embodiments, the farthest position of the component away from the isocenter may be determined manually by a user. In 625, the trajectory updating module 430 may also determine whether the updated iteration number for distance, N1, is greater than a second threshold (represented by thr2). In some embodiments, the second threshold may be a predetermined value, e.g., 5, 10, 15, 20. In some embodiments, the second threshold may be determined by the trajectory updating module 430.

In responding to the determination that the updated distance, D1, is not greater than the first threshold and the updated number of distance iteration, N1, is not greater than the second threshold, process 600 may proceed to step 630. In 630, the collision detection module 420 may determine whether the collision is still likely to occur. If the collision detection module 420 determines that the collision is still likely to occur, process 600 may loop back to step 620 to update the distance between the component and the isocenter. For example, process 600 may update the distance between the component and the isocenter by adding a distance increment. Accordingly, the iteration number for distance may be then added by 1. To facilitate describing the process, in 620, the distance increment in different iterations is represented by the same "i." It should be noted that, in some embodiments, the distance increment added in each iteration may be the same. In some embodiments, the distance increment added in each iteration may be different. Process 600 may then perform operations described in connection with step 625 and step 630. On the other hand, if the collision detection module 420 determines that the collision is not likely to occur, process 600 may end in 665.

In responding to the determination that the updated distance, D1, is greater than the first threshold or the updated iteration number for distance, N1, is greater than the second threshold, process 600 may proceed to step 635. In 635, the trajectory updating module 430 may set the distance between the component and the isocenter 709 as the first threshold. In 635, the trajectory updating module 430 may further set the number of orientation iteration(s), N2, as "0."

In 640, the collision detection module 420 may determine whether the collision is still likely to occur. If the collision detection module 420 determines that the collision is not likely to occur, process 600 may end in 665. On the other hand, if the collision detection module 420 determines that the collision is still likely to occur, process 600 may proceed to step 645.

In 645, the trajectory updating module 430 may determine an updated orientation of the component. The orientation refers to an angle of the component relative to a tangent of the trajectory at the corresponding position of the component. The orientation may be updated by adding an orientation increment (represented by j), i.e., A=A+j. The orientation increment, j, may be set automatically by, for example, the trajectory updating module 430 or manually by a user. In some embodiments, the value of the orientation increment may be any suitable value from 0 to 90 degrees.

In some embodiments, the value of the orientation increment may be from 0.1 degree to 10 degrees, from 10.1 degree to 20 degrees, from 20.1 degree to 30 degrees, from 30.1 degree to 40 degrees, from 40.1 degree to 50 degrees, from 50.1 degree to 60 degrees, from 60.1 degree to 70 degrees, from 70.1 degree to 80 degrees, from 80.1 degree to 90 degrees. Accordingly, the number of orientation iteration may be updated by adding "1," i.e., N2=N2+1.

In 650, the trajectory updating module 430 may determine whether the updated orientation is greater than a third threshold (represented by thr3). The third threshold may be determined based on the largest orientation of the component. In some embodiments, the largest orientation of the component may be determined according to the physical construction of the component. Alternatively or additionally, the largest orientation of the component may be determined manually by a user. For example, the third threshold may be determined as 90 degrees. In 650, the trajectory updating module 430 may also determine whether the updated iteration number for orientation, N2, is greater than a fourth threshold (represented by thr4). In some embodiments, the fourth threshold may be a predetermined value, e.g., 5, 10, 15, or 20. In some embodiments, the fourth threshold may be determined automatically by the trajectory updating module 430.

In responding to the determination that the updated orientation is not greater than the third threshold and the updated number of orientation iteration is not greater than the fourth threshold, process 600 may proceed to step 655 and determine whether the collision is still likely to occur. If the collision detection module 420 determines that the collision is still likely to occur, process 600 may loop back to step 645 to update the orientation of the component. For example, process 600 may update the orientation of the component by adding an orientation increment. Accordingly, the iteration number for orientation may be then added by "1." To facilitate describing the process, in 645, the orientation increment in different iterations is presented by the same "j." It should be noted that, in some embodiments, the orientation increment added in each iteration may be the same. In some embodiments, the orientation increment added in each iteration may be different. Process 600 may then perform operations described in connection with steps 650 and 655. On the other hand, if the collision detection module 420 determines that the collision is not likely to occur, process 600 may end in step 665.

In responding to the determination that the updated orientation is greater than the third threshold and/or the updated number of orientation iteration is greater than the fourth threshold, process 600 may proceed to step 660. In 660, the trajectory updating module 430 may set the orientation as the third threshold. Then process 600 proceeds to step 665 and end.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, in 635, the trajectory updating module 430 may not set the distance between the component and the isocenter to be the first threshold. The trajectory updating module 430 may set the distance to be the initial distance between the component and the isocenter. As another example, in 660, the trajectory updating module 430 may not set the orientation of the component to be the third threshold. The trajectory updating module 430 may set the orientation to be the initial orientation of the component. In some embodiments, the trajectory updating module 430 may first adjust the orientation of the component, and then adjust the distance between the component and the isocenter. In some embodiments, the trajectory updating module 430 may adjust the orientation of the component and the distance between the component and the isocenter, simultaneously. In some embodiments, steps 610 and 615 may be performed before step 605.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A system, comprising:
a storage device storing a set of instructions; and
at least one processor in communication with the storage device, wherein when executing the set of instructions, the at least one processor is configured to cause the system to:
obtain a first position of a component of a medical device;
determine whether a collision is likely to occur between the component and a subject at the first position;
in response to the determination that the collision is likely to occur between the component and the subject at the first position, at least determine a second position for the component that is different from the first position;
wherein the component and an isocenter of the medical device are arranged at a first distance at the first position, and the component and the isocenter of the medical device are arranged at a greater distance than the first distance at the second position;
move the component from the first position to the second position; and
determine an image of a target subject, wherein to determine an image of a target subject, the at least one processor is further configured to cause the system to:
generate a virtual scalable projection image on the first position based on ray-information on the second position and a scale transformation; and
reconstruct the image based on the virtual scalable projection image.

2. The system of claim 1, wherein to determine whether the collision is likely to occur between the subject and the component, the at least one processor is further configured to cause the system to:
determine, before, during or after a movement of the component, whether the collision is likely to occur between the subject and the component.

3. The system of claim 1, in response to the determination that the collision is likely to occur between the component and the subject at the first position, the at least one processor is configured to further cause the system to:

determine an updated distance between the component and the isocenter by adding a distance increment to the first distance automatically or manually.

4. The system of claim 1, wherein the at least one processor is further configured to cause the system to:
determine one or more parameters associated with the component, the one or more parameters including at least one of a velocity, a moving direction, a position, or an accelerated velocity.

5. The system of claim 1, wherein the first position is one of a plurality of initial positions in a predetermined initial trajectory of the component.

6. The system of claim 5, wherein the at least one processor is further configured to cause the system to:
update at least one of the plurality of initial positions of the component in the predetermined initial trajectory of the component to determine an updated trajectory of the component.

7. The system of claim 6, wherein the at least one processor is further configured to cause the system to:
update the initial trajectory using a machine-learning technique.

8. The system of claim 1, wherein to generate a virtual scalable projection image on the first position based on ray-information on the second position and a scale transformation, the at least one processor is further configured to cause the system to:
obtain ray-information on the first position by scaling the ray-information on the second position; obtain an interpolated ray-information of the ray-information on the first position; and
generate the virtual scalable projection image on the first position based on the ray-information and the interpolated ray-information.

9. The system of claim 1, wherein the medical device includes a Cone Beam Computed Tomography device and/or a radiotherapy (RT) device.

10. The system of claim 1, wherein the component has a first orientation at the first position, and the at least one processor is further configured to cause the system to:
determine a second orientation for the component that is different from the first orientation, wherein the component has the second position at the second orientation.

11. The system of claim 10, wherein to determine a second orientation for the component that is different from the first orientation, the at least one processor is further configured to cause the system to:
update a distance between the component and the isocenter;
determine the updated distance between the component and the isocenter at the second position;
determine whether the updated distance is larger than a threshold;
in response to a determination that the updated distance is larger than the threshold, set the updated distance between the component and the isocenter as the threshold;
determine whether a collision is likely to occur between the component and the subject at the second position;
in response to a determination that the collision is likely to occur between the component and the subject at the second position, update an orientation of the component until no collision is likely to occur between the component and the subject; and
designate the updated orientation as the second orientation.

12. A method implemented on a system, the system including at least one processor and a storage device, the method comprising:
obtaining a first position of a component of a medical device;
determining whether a collision is likely to occur between the component and a subject at the first position;
in response to the determination that the collision is likely to occur between the component and the subject at the first position, at least determining a second position for the component that is different from the first position; wherein the component and an isocenter of the medical device are arranged at a first distance at the first position, and the component and the isocenter of the medical device are arranged at a greater distance than the first distance at the second position;
moving the component from the first position to the second position; and
determining an image of a target subject, including:
generating a virtual scalable projection image on the first position based on ray-information on the second position and a scale transformation; and
reconstructing the image based on the virtual scalable projection image.

13. The method of claim 12, in response to the determination that the collision is likely to occur between the component and the subject at the first position, further comprising:
determining an updated distance between the component and the isocenter by adding a distance increment to the first distance automatically or manually.

14. The method of claim 12, further comprising:
determining one or more parameters associated with the component, the one or more parameters including at least one of a velocity, a moving direction, a position, or an accelerated velocity.

15. The method of claim 12, wherein the first position is one of a plurality of initial positions in a predetermined initial trajectory of the component.

16. The method of claim 15, further comprising:
updating the initial trajectory using a machine-learning technique.

17. The method of claim 12, wherein the generating a virtual scalable projection image on the first position based on ray-information on the second position and a scale transformation includes:
obtaining ray-information on the first position by scaling the ray-information on the second position; obtaining an interpolated ray-information of the ray-information on the first position; and
generating the virtual scalable projection image on the first position based on the ray-information and the interpolated ray-information.

18. A non-transitory computer readable medium embodying a computer program product, the computer program product comprising instructions configured to cause a computing system to:
obtain a first position of a component of a medical device;
determine whether a collision is likely to occur between the component and a subject at the first position;
in response to the determination that the collision is likely to occur between the component and the subject at the first position, at least determine a second position for the component that is different from the first position; wherein the component and an isocenter of the medical device are arranged at a first distance at the first position, and the component and the isocenter of the medical device are arranged at a greater distance than the first distance at the second position;

move the component from the first position to the second position; and determine an image of a target subject, wherein to determine an image of a target subject, the instructions are configured to cause the computing system further to:

generate a virtual scalable projection image on the first position based on ray-information on the second position and a scale transformation; and reconstruct the image based on the virtual scalable projection image.

* * * * *